United States Patent [19]

Siddons

[11] 3,994,300

[45] Nov. 30, 1976

[54] EPILATION BY ELECTRICAL DISCHARGE

[75] Inventor: James Eric Siddons, Mississauga, Canada

[73] Assignee: Lawrence Peska Associates, Inc., New York, N.Y. ; a part interest

[22] Filed: July 11, 1975

[21] Appl. No.: 595,367

[52] U.S. Cl............................. 128/303.18; 219/223; 219/384
[51] Int. Cl.²..................... A61B 17/40; A61N 3/04
[58] Field of Search.................. 128/303.18, 303.13, 128/303.14, 303.17, 303.19, 404, 419 R, 421; 219/223, 384

[56] References Cited
UNITED STATES PATENTS

| | | | |
|---|---|---|---|
| 1,210,316 | 12/1916 | Hollingshead | 128/303.18 |
| 1,731,627 | 10/1929 | Johnson et al. | 128/303.18 |
| 2,888,927 | 6/1959 | Fozard | 128/303.13 |
| 3,054,405 | 9/1962 | Tapper | 128/303.18 |
| 3,614,382 | 10/1971 | Politzer | 128/303.14 |
| 3,815,603 | 6/1974 | Sramek | 128/303.18 |

FOREIGN PATENTS OR APPLICATIONS

| | | | |
|---|---|---|---|
| 629,091 | 4/1936 | Germany | 128/303.13 |
| 243,478 | 1/1947 | Switzerland | 128/303.18 |

Primary Examiner—Robert W. Michell
Assistant Examiner—Lee S. Cohen
Attorney, Agent, or Firm—Jack D. Slobod

[57] ABSTRACT

An epilating device includes an electrically conductive grid adapted to be placed against the skin, to serve as a ground plane, and an array of needle electrodes spaced behind the grid in register with openings in the grid for setting up electrical discharges between the ends of the needle electrodes and the ends of previously shaved hair shafts protruding through the grid to erode the hair shaft and damage the hair follicle. In one embodiment adapted to set up a discharge through the longest hairs protruding through the grid, the needle electrodes are connected in common to a capacitor. In another embodiment adapted to set up simultaneous discharges to each of the hair shafts protruding through the grid, the electrodes are connected to individual capacitors.

5 Claims, 6 Drawing Figures

U.S. Patent     Nov. 30, 1976     3,994,300

EPILATION BY ELECTRICAL DISCHARGE

FIELD OF THE INVENTION

The present invention relates generally to epilation by electrolysis. In its particular aspects the present invention relates to the provision of pointed electrodes spaced above the ends of hair shafts for creating electrical discharges through the hair shafts.

BACKGROUND OF THE INVENTION

In the prior art it is well known to remove hair by an electrolysis technique wherein a needle probe is inserted through the epidermis and dermis of the patient to reach a hair follicle. Then a high voltage is applied between the probe and the epidermis to destroy the hair follicle. The difficulty with this prior art technique is that considerable pain is caused by insertion of the needle into the tissue of the patient.

OBJECTS OF THE INVENTION

It is an object of the present invention to provide an electrical epilatory device in which no probes are inserted into the tissue of the patient.

It is a further object of the present invention to provide an epilatory device for simultaneously removing plural hairs.

It is yet another object of the present invention to provide an electrical discharge epilatory device which may be utilized in a manner similar to an electric razor.

SUMMARY OF THE INVENTION

Briefly, the aforementioned and other objects of the present invention are satisfied by providing an electrical discharge epilating device in a housing having a handle. The underside of the housing comprises a perforate conductive sheet or grid adapted to be placed against a previously shaved epidermis area. Short hair shafts are received through the perforations in the underside and an array of needle electrodes are provided within the housing spaced behind the underside in register with the perforations. Capacitor means are connected between the needles and the housing underside and are charged with sufficient voltage to generate an electrical discharge between the points of the needles and the ends of the hair shafts projecting through the perforated underside of the housing. As a result, an electric current is carried down the hair shaft to the hair follicle for destroying the follicle and spark eroding the hair shaft. In one embodiment the needle electrodes are connected in common to a capacitor, while in another embodiment individual capacitors are provided connected to individual needle electrodes.

Other objects, features and advantages of the present invention will become apparent upon perusal of the following detailed description of two embodiments thereof when taken in conjunction with the appended drawing wherein.

DETAILED DESCRIPTION

Figures 1, 2:
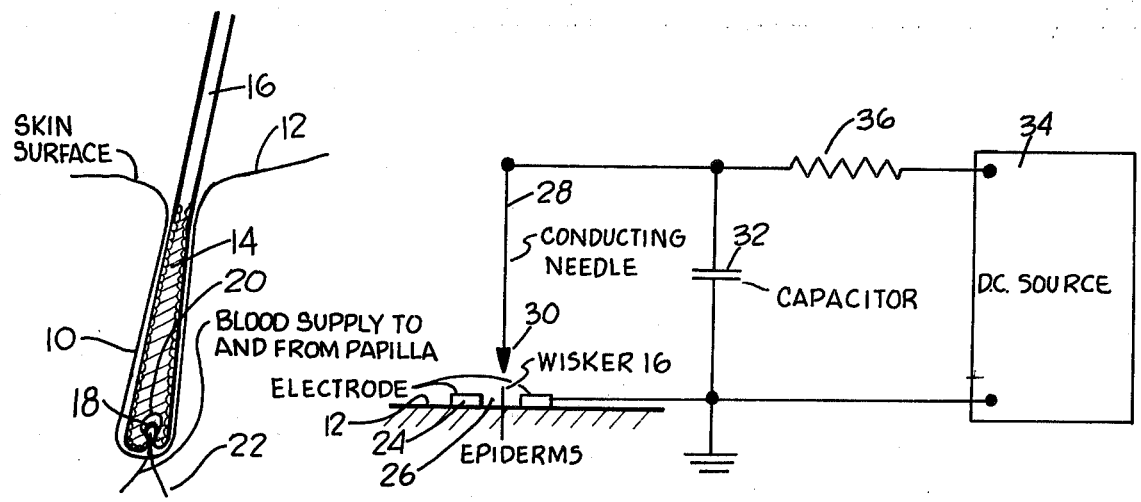
FIG. 1 is a cross-sectional elevation view of a hair follicle.
FIG. 2 is an electrical schematic for the epilating method of the present invention.

Referring to FIG. 1 for background purposes, a hair follicle 10 comprises a sack below the surface of the skin 12 which contains an elongated body of soft keratin 14 which is extruded in the growth process to form the hard keratin of the hair shaft 16 projecting above skin surface 12. A small bulb 18 at the bottom of the soft keratin body 14, termed the papilla, is surrounded by a germinative layer 20 and receives blood vessels 22. The destruction of follicle 10 is accomplished by damaging either papilla 18 or germinative layer 20.

If the hair shaft 16, which is normally of high dielectric strength, could be caused to conduct an electrical current this current could be carried down through the soft keratin 14 to papilla 18 and germinative layer 20 for damaging them. There is evidence that conduction through hair shaft 16 can be accomplished. For example, there are reported instances in which a lineman, who received considerable electrostatic charge during his work, had hair on his arms permanently removed thereby. While obviously, the electrical potential in such a case was extremely high it is believed that it is possible to achieve similar results at reduced potentials.

Now referring to FIG. 2, according to the technique of the present invention, epidermis layer 12 is first closely shaved to provide relatively short, predictably uniform length whisker hair shafts 16 projecting therefrom. Then a flat apertured sheet electrode 24 is placed against skin surface 12 with hair shaft 16 projecting through aperture 26 in electrode 24. A needle electrode 28 having a pointed end 30, for high field strength at modest potentials is spaced very closely above the free end of hair shaft 16. Pointed end 30 is maintained approximately 1 millimeter above the end of hair shaft 16 so that a small potential, such as 1,000 volts, applied between needle electrode 28 and sheet electrode 24 will generate an electrical arc or discharge between pointed end 30 and the free end of hair shaft 16 to conduct a current through the hair shaft into follicle 10. The production of an arc has the additional advantage of shortening hair shaft 16 by spark erosion or burning.

To supply an instanteously high electrical current to the hair shaft 16, a charge storage means such as capacitor 32 is connected between electrodes 28 and 24. The capacitor is charged and recharged from a D. C. source 34 via a series resistor 36. The time constant of resistor 36 and capacitor 32 is adjusted for limiting the power supplied through hair shaft 16 to a safe relatively pain free level.

Figure 3:
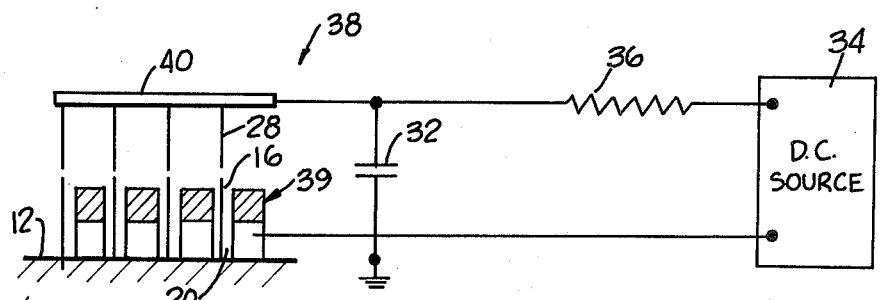
FIG. 3 is an electrical schematic of one embodiment of an epilating device.

Now referring to FIG. 3, according to a first embodiment 38 of the epilating device of the present invention adapted to operate upon plural hair shafts 16 sequentially, a grid or perforated sheet 39 having plural apertures 20 is placed against skin surface 12 for receiving hair shafts 16. Plural needle electrodes 28, maintained spaced above hair shafts 16 are suspended from a common bus bar 40 in registry with perforations 20. Bus bar 40 is connected to one end of capacitor 32. The opposite end of capacitor 32 is connected to grid 39 which forms a ground plane on skin surface 12. Capacitor 32 is charged as in FIG. 2 from D. C. source 34 via resistor 36.

In embodiment 38, since the needle electrodes 28 are commoned by bus bar 40, electrical discharges will be set up in the easiest path to the longest of hair shafts 16, necessitating that the electrodes 28 and 40 be maintained in a fixed position on skin surface 12 while the longest hairs are burned to a shorter length so that discharges may be then initiated to the next longest hair shaft 16.

Figures 4, 5, 6:
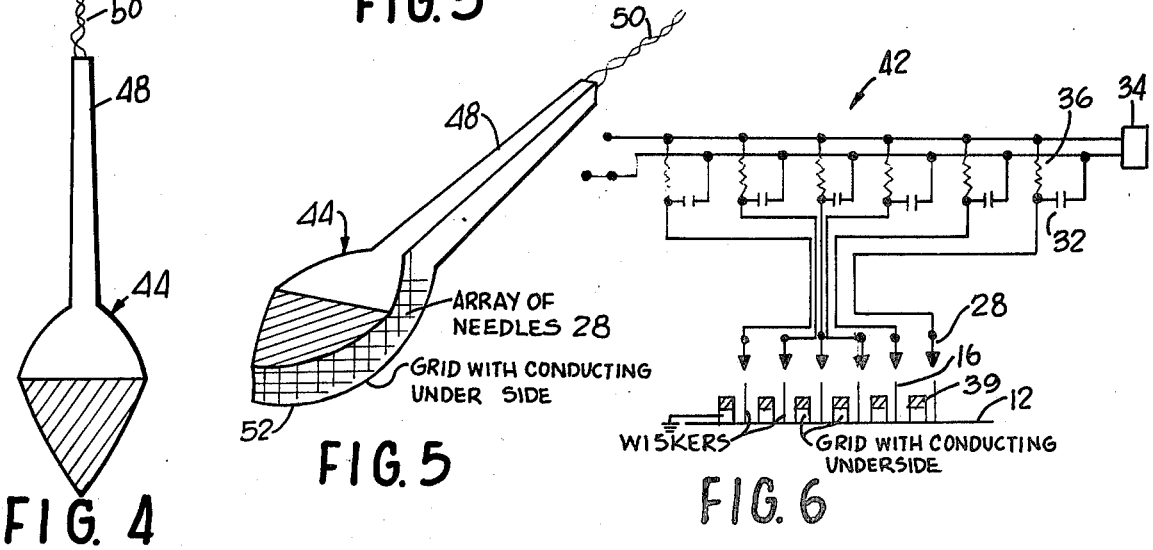
FIG. 4 is a mechanical top view of the epilating device of the present invention.
FIG. 5 is a pictorial presentation generally in side elevation of the epilating device in FIG. 4.
FIG. 6 is an electrical schematic similar to FIG. 3 but of an alternate embodiment epilating device.

To obviate the need to maintain the electrodes 39 and 40 in a fixed position along the skin surface 12, the alternate embodiment 42 in FIG. 6 is utilized. Therein the bus bar 40 is not utilized. Instead the plural needle electrodes 28 are connected individually to plural corresponding capacitors 32 which are separately charged by plural corresponding resistors 36 leading to source 34. The ends of capacitors 32 remote from needles 28 are each connected to electrode 39. Thus, the separately chargeable capacitors 32 connected to each needle electrode 28 allow for simultaneous discharges to occur between each needle electrode 28 and the free end of each hair shaft 16 spaced below the needle.

Referring to FIGS. 4 and 5, the embodiments 38 or 42 are conveniently packaged in a lightweight bulbous housing 44 which includes an elongated straight handle 48 out of the end of which is passed a cable 50 leading to D. C. source 34. The underside 52 of bulbous housing 44 comprises the perforate electrically conducting sheet or grid 39 which is pressed against the surface of the skin. The array of needle electrodes 28, the capacitors 32 and resistors 36 may be contained in housing 44 or alternatively may be packaged separately along with D. C. source 34, in order to reduce the bulk of housing 44.

Having described two embodiments of the present invention in great detail, it should be apparent that numerous modifications, additions and omissions in the details thereof are possible within the intended spirit and scope of the invention. Hence, the following claims define the scope of the invention.

What is claimed is:
1. An epilating device comprising a perforated electrically conductive sheet adapted to be placed against the skin, the perforations being of a size to receive hair shafts therethrough, an array of electrodes having operative pointed ends spaced on one side of the sheet in register with the perforations, and electric charge storage means connected between said electrodes and said conductive sheet, for storing charge at sufficient voltage to form an electrical discharge from the pointed end of an electrode to an end of a hair shaft projecting through a perforation.
2. The device of claim 1 further comprising means for connecting said electrodes in common to said charge storage means.
3. The device of claim 1 wherein said charge storage means comprises a separate capacitor connected between each electrode and said sheet.
4. The device of claim 3 further comprising means for charging said charge storage means.
5. The device of claim 1 further comprising means for charging said charge storage means.

* * * * *